United States Patent
Zhang et al.

(10) Patent No.: US 9,724,213 B2
(45) Date of Patent: Aug. 8, 2017

(54) NANOCRYSTALLINE CELLULOSE MATERIALS AND METHODS FOR THEIR PREPARATION

(71) Applicant: WASHINGTON STATE UNIVERSITY, Pullman, WA (US)

(72) Inventors: Xiao Zhang, Richland, VA (US); Elvie Escorrow Brown, Pasco, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 14/443,867

(22) PCT Filed: Nov. 19, 2012

(86) PCT No.: PCT/US2012/065927
§ 371 (c)(1),
(2) Date: May 19, 2015

(87) PCT Pub. No.: WO2014/077854
PCT Pub. Date: May 22, 2014

(65) Prior Publication Data
US 2015/0297371 A1    Oct. 22, 2015

(51) Int. Cl.
*A61F 2/82* (2013.01)
*C12P 19/04* (2006.01)
(Continued)

(52) U.S. Cl.
CPC ............. *A61F 2/82* (2013.01); *A61L 27/225* (2013.01); *A61L 27/48* (2013.01); *A61L 27/507* (2013.01); *A61L 31/046* (2013.01); *C07G 1/00* (2013.01); *C08B 15/00* (2013.01); *C08B 15/005* (2013.01); *C08B 15/02* (2013.01); *C08B 15/05* (2013.01); *C08B 37/0021* (2013.01); *C08B 37/0057* (2013.01); *C08H 1/00* (2013.01); *C08H 6/00* (2013.01); *C08H 8/00* (2013.01);
(Continued)

(58) Field of Classification Search
None
See application file for complete search history.

(56) References Cited

U.S. PATENT DOCUMENTS 5,272,074 A    12/1993    Rubens
5,510,077 A    4/1996    Dinh et al.
(Continued)

FOREIGN PATENT DOCUMENTS

JP    2006238728 A    9/2006

OTHER PUBLICATIONS

Olsson, bioethano production from lignocellulosic material, center for microbial biotechnology biocentrum—DTU, Denmark Polysaccharides: Structural Diversity and Functional Versatility, 2004, Second Edition, Chapt 42, p. 961.*
(Continued)

*Primary Examiner* — Melvin C Mayes
*Assistant Examiner* — Stefanie Cohen
(74) *Attorney, Agent, or Firm* — Pepper Hamilton LLP

(57) ABSTRACT

Disclosed herein are methods for producing nanocrystalline cellulose and oxidized nanocrystalline cellulose from biomass. Also disclosed are methods for forming materials, and the materials formed from a fibrin matrix that incorporates the nanocrystalline cellulose and/or the oxidized nanocrystalline cellulose.

14 Claims, 7 Drawing Sheets

(51) Int. Cl.

| | | |
|---|---|---|
| C07G 1/00 | (2011.01) | |
| C08B 15/00 | (2006.01) | |
| C08B 15/02 | (2006.01) | |
| C08B 15/05 | (2006.01) | |
| C08B 37/02 | (2006.01) | |
| C08B 37/00 | (2006.01) | |
| C08H 1/00 | (2006.01) | |
| C08H 7/00 | (2011.01) | |
| C08H 8/00 | (2010.01) | |
| C08L 1/02 | (2006.01) | |
| C08L 1/04 | (2006.01) | |
| C08L 89/00 | (2006.01) | |
| A61L 27/22 | (2006.01) | |
| A61L 27/48 | (2006.01) | |
| A61L 27/50 | (2006.01) | |
| A61L 31/04 | (2006.01) | |
| C12P 21/00 | (2006.01) | |
| C13K 1/02 | (2006.01) | |

(52) U.S. Cl.
CPC ...... *C08L 1/02* (2013.01); *C08L 1/04* (2013.01); *C08L 89/00* (2013.01); *C12P 19/04* (2013.01); *C12P 21/005* (2013.01); *C13K 1/02* (2013.01); *A61F 2230/0069* (2013.01); *A61L 2400/04* (2013.01); *A61L 2400/12* (2013.01)

(56) References Cited

U.S. PATENT DOCUMENTS

| | | | |
|---|---|---|---|
| 5,660,873 | A | 8/1997 | Nikolaychik et al. |
| 5,769,934 | A * | 6/1998 | Ha .................... C08B 15/02 106/162.8 |
| 5,788,812 | A | 8/1998 | Agar et al. |
| 5,849,034 | A | 12/1998 | Schwartz |
| 7,029,689 | B2 | 4/2006 | Berglund et al. |
| 8,192,348 | B2 | 6/2012 | Tranquillo et al. |
| 2003/0013163 | A1 | 1/2003 | Klemm et al. |
| 2003/0219466 | A1 | 11/2003 | Kumta et al. |
| 2004/0115176 | A1 | 6/2004 | Swartz et al. |
| 2006/0094320 | A1 | 5/2006 | Chen et al. |
| 2010/0041148 | A1 | 2/2010 | Bertholdt |
| 2010/0042197 | A1 | 2/2010 | Bodin et al. |
| 2011/0033927 | A1 | 2/2011 | Rolle et al. |
| 2011/0198533 | A1 | 8/2011 | Nachtkamp et al. |

OTHER PUBLICATIONS

Moon et al, cellulose nanomaterials review: structure, properties and nanocomposites, 2011, chem soc review, 40, pp. 3941-3994.*

Filpponen et al, photoresponsive cellulose nanocrystals, 2011, intech, pp. 34-43.*

Backdahl et al., Mechanical properties of bacterial cellulose and interactions with smooth muscle cells, *Biomaterials* (Nov. 28, 2005), 27(9):2141-2149.

Brown et al., Never-Dried BC/fibrin composites: preparation, morphology and mechanical properties, Cellulose (Feb. 3, 2011), 18:631-641.

Hamad, et al., Structure-process-yield interrelations in nanocrystalline cellulose extraction, *Canadian Journal of Chemical Engineering* (Jun. 2010), 88(3):392-402.

Hamad, On the development and applications of cellulosic nanofibrillar and nanocrystalline materials, *The Canadian Journal of Chemical Engineering* (Oct. 2006), 84(5):513-519.

Klemm et al., Bacterial synthesized cellulose—artificial blood vessels for microsurgery, *Progress in Polymer Science* (2001), 26(9):1561-1603.

Sturcova, et al., Elastic Modulus and Stress-Transfer Properties of Tunicate Cellulose Whiskers, *Biomacromolecules* (Feb. 15, 2005), 6:1055-1061.

International Search Report and Written Opinion for International Application No. PCT/US2012/065927 mailed May 21, 2013.

Abraham et al., Extraction of nanocellulose fibrils from lignocellulosic fibres: A novel approach, *Carbohydrate Polymers* (Jun. 21, 2011), 86:1468-1475.

Glaesemann, Ovalbumin-Based Scaffolds Reinforced with Cellulose Nanocrystals for Bone Tissue Engineering, Thesis for Master of Science in Materials Science and Engineering, pp. 1-78 (Jun. 24, 2011).

Habibi et al., Cellulose Nanocrystals: Chemistry, Self-Assembly, and Applications, *Chem Rev* (Jun. 9, 2010), 110(6):3479-3500.

Hu et al., Feedstock Pretreatment Strategies for Producing Ethanol from Wood, Bark and Forest Residues, *BioResources* (2008), 3(1):270-294.

Jockenhoevel et al., Fibrin gel—advantages of a new scaffold in cardiovascular tissue engineering, *European Journal of Cardiothoracic Surgery* (Apr. 2001), 19(4):424-430.

Materials Inspired by Mother Nature: A 1-pound boat that could float 1,000 pounds, accessed at https://web.archive.org/web/20120428131214/http://www.nanowerk.com/news/newsid=24702.php, Mar. 25, 2012, pp. 1-5.

Rosa et al., Cellulose nanowhiskers from coconut husk fibers: Effect of preparation conditions on their thermal and morphological behavior, *Carbohydrate Polymers* (Feb. 10, 2010), 81(1):83-92.

Siqueira et al., Cellulosic Bionanocomposites: A Review of Preparation, Properties and Applications, *Polymers* (Dec. 13, 2010), 2:728-765.

* cited by examiner

Figure 1: An integrated wheat straw bioconversion process to produce nanocrystalline cellulose in high yield

NANOCRYSTALLINE CELLULOSE MATERIALS AND METHODS FOR THEIR PREPARATION

CLAIM OF PRIORITY

This application is a U.S. national stage filing under 35 U.S.C. §371 of International Application No. PCT/US2012/065927 filed Nov. 19, 2012 entitled "NANOCRYSTALLINE CELLULOSE MATERIALS AND METHODS FOR THEIR PREPARATION", which is incorporated herein by reference.

BACKGROUND

Cellulose is the structural component of the primary cell wall of green plants, many forms of algae and the oomycetes, and is the most common organic compound on the earth. Cellulose is a polysaccharide consisting of a linear chain of several hundred to over ten thousand $\beta(1\rightarrow4)$ linked D-glucose units. The basic units of cellulose are nanocellulose fibrils that are formed of an in intermixing of areas of disordered structural regions and crystalline structural regions. Isolated crystalline structural regions, or nanocrystalline cellulose (NCC), are very strong and have a strength to weight ratio that is better than stainless steel.

Nanocrystalline cellulose is lightweight, conducts electricity, is as strong as Kevlar, is not harmful to humans, and is available from plant sources. However, a number of technical bottlenecks hinder a cost effective production of NCC. Production of NCC requires expensive starting materials, for example, bleached pulp or microcrystalline cellulose, to produce high quality NCC. The crystallinity of most starting material is also below 55%. In addition, since concentrated mineral acids are used to hydrolyze non-crystalline cellulose to soluble sugars, more than half of the initial materials are wasted in the production process. The huge consumptions of inorganic acid and subsequent neutralization agents represent another major economical bottleneck in NCC production. Cost factors have significantly limited commercial production and therefore applications of NCC, and there remains a need for improved processes for the production of high-quality NCC.

There may be many future applications for NCC. Because of its strength, NCC may be usable as a replacement for metal and plastic parts and could make non-organic plastics obsolete. Because of the unique properties of NCC, promising commercial applications may be developed in many industrial sectors including paints, coatings, textiles, polymer composites and cosmetics. In addition, NCC may also be applicable to biological uses as well. For example, many different tissues may be repaired by grafting, including: skin, bone, nerve, tendon, blood vessel, fat and cornea tissues. Grafting refers to a surgical procedure to move tissue from one site to another on the body, or from one body to another, or to repair tissue with synthetic substitutes. As an example, skin grafting is often used to treat skin loss due to wounds, burns, infections or surgeries. In the case of damaged skin, the damaged portion is removed, and new skin is grafted in its place. Skin grafting can reduce the course of treatment and hospitalization needed, and can also improve function and appearance. Vascular grafting is the use of transplanted or prosthetic blood vessels to repair damaged, or clogged blood vessels in surgical procedures.

Autologous vessel grafts, or those that are taken from other vascular parts of the patient, have typically been the only replacement grafts that have great long-term success on implantation. However, the body has only a limited supply of usable vessels for grafting, especially when one needs multiple bypasses. The two most common synthetic vascular graft materials; polytetrafluoroethylene (PTFE) and polyethylene terephthalate (PET), are generally only suitable for grafts having diameters larger than about 6 mm. Synthetic materials for the replacement of small-diameter vascular grafts (e.g. coronary, renal, and carotid) generally do not have suitable biological and mechanical properties.

Biological and mechanical compliance are the two most critical properties required for artificial vascular grafts, and this typically applies to other tissue grafts as well. The material should be biocompatible and should possess mechanical properties that mimic those of the native tissue. For vasculature, synthetic grafts should have both strength and elasticity to withstand the pulsatile pressures of the physiological environment. A common limitation of existing materials is the failure to provide long-term functionality, as typical vascular grafts either, became blocked with blood clots due to biological incompatibility, or disintegrate due to lack of mechanical strength.

There remains a need for the development of improved synthetic tissues for tissue grafts, and in particular for vascular grafts, such as small diameter grafts. Synthetic materials, in particular for vascular grafts, should have a strength and elasticity comparable to that of the tissue being repaired, and should have a biocompatibility with the tissue being repaired.

SUMMARY

A method for producing cellulose nanocrystals has been provided which allows for the production of better quality nanocrystals at a reduced cost, and with less waste. In addition, a biomaterial of cellulose nanocrystals cross-linked into a fibrin matrix has been produced to provide a synthetic material with improved properties for use as a grafting material.

In an embodiment, a method for producing nanocrystalline cellulose from biomass includes extracting hemi-cellulose from the biomass to produce a first biomass portion and a first extract, extracting lignin from the first biomass portion to produce a cellulose portion and a second extract, processing the cellulose portion into cellulose nanofibrils, the nanofibrils comprising nanocrystalline cellulose separated by regions of amorphous cellulose, hydrolyzing the amorphous cellulose in the nanofibrils to produce a solution of nanocrystalline cellulose and glucose, separating the nanocrystalline cellulose from the glucose, and recycling at least one of: the first extract, the second extract and the glucose.

In an embodiment, a method for producing a graft for repair of biological tissue includes mixing an aqueous solution of nanocrystalline cellulose, fibrinogen and thrombin to produce a reactive mixture, and incubating the reactive mixture to convert fibrinogen to fibrin and produce a nanocomposite material of cross-linked nanocrystalline cellulose and fibrin.

In an embodiment, a nanocomposite matrix material comprising a fibrin matrix reinforced with oxidized nanocrystalline cellulose through cross-linking.

In an embodiment, a nanocomposite matrix material comprising a fibrin matrix reinforced with nanocrystalline cellulose through cross-linking.

In an embodiment, a graft for repair of a blood vessel includes a formed tubular fibrin matrix reinforced with nanocrystalline cellulose through cross-linking.

DETAILED DESCRIPTION

Figure 1:
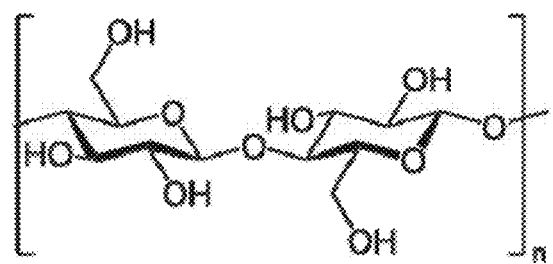
FIG. 1 depicts a representation of the structure of cellulose according to an embodiment.
Figure 2:
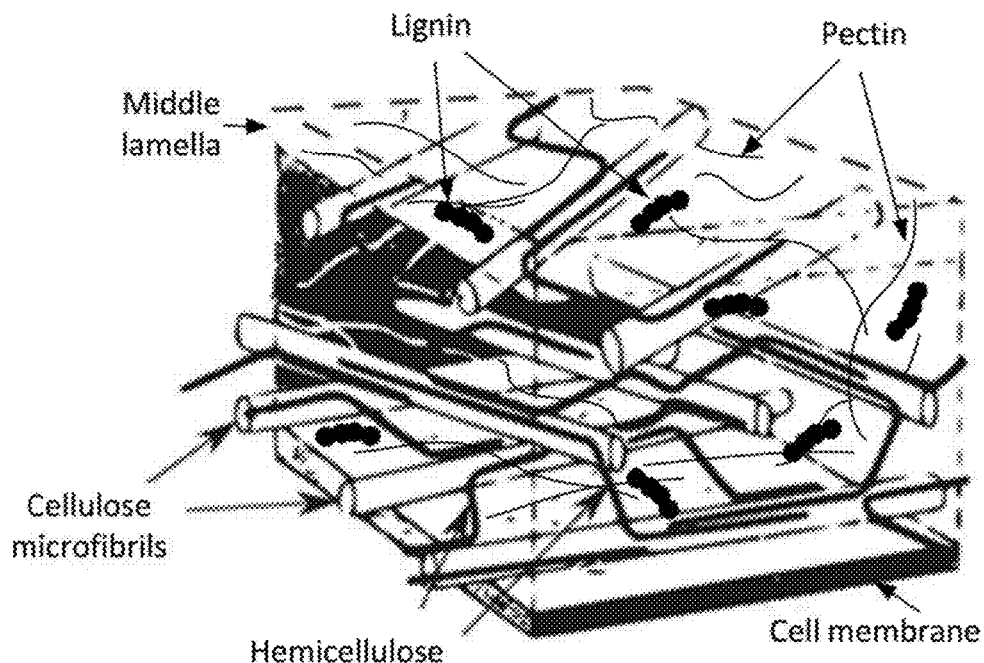
FIG. 2 is a simplified illustration of a cut-away view of a plant cell according to an embodiment.

Cellulose, the structure of which is illustrated in FIG. 1, is a widely available and renewable material as it is found in the cell walls of plants and bacterial cells. As represented in FIG. 1, cellulose is a biomolecule of repeating glucose units that are arranged linearly and are linked together by β-1,4 linkages to form long chains. The primary commercial source for cellulose is plants, which, as shown in FIG. 2, are essentially a network of cellulose microfibrils held together by a matrix of hemicellulose, pectin and lignin. Cellulose has strength, but is lacking elasticity, and therefore also lacks the appropriate mechanical properties specifically required for synthetic grafts, such as, for example, a vascular graft.

Figure 3:
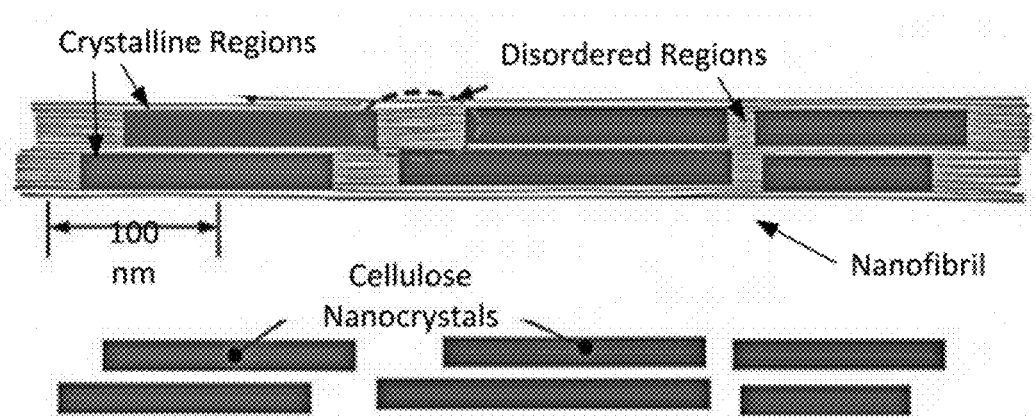
FIG. 3 is a representative cross-section of a cellulose nanofibril with nanocrystals according to an embodiment.
Figure 4:
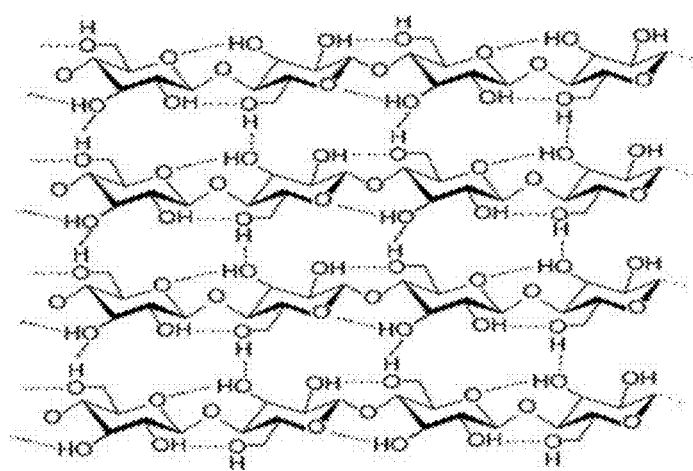
FIG. 4 is a representative cross-section of a cellulose nanocrystal structure according to an embodiment.

Cellulose nanocrystals have been isolated from cellulose and have been determined to have an exceptional strength to weight ratio. Cellulose nanocrystals may be isolated from cellulose microfibrils which are bundles of elementary cellulose nanofibrils. FIG. 3 depicts a representative nanofibril. Within these nanofibrils are regions which are very well ordered, cellulose nanocrystals, in which cellulose chains are closely packed in parallel with one another and are held together by hydrogen bonds as shown in FIG. 4. Typically, several of these nanocrystalline regions appear along a single nanofibril, and are separated by amorphous regions which do not exhibit a large degree of order.

Nanocrystalline cellulose (NCC) is the nano-size form of cellulose, and its ultra-small size provides an inherent strength-reinforcing capability that is significantly greater than native cellulose. NCC has a strength-to-weight ratio that is greater than that of steel. In addition, NCC may be drawn into a thin film like layer and may be produced in a variety of colors. NCC may be obtained from a variety of sources, including plants, animals and microorganisms. The crystal structure dimensions of NCCs differ depending on the source, and crystal nanowhiskers may, for example, have approximate dimensions of about 100 to about 2000 nm in length by about 2 to about 50 nm lateral to the length dimension.

Figure 5:
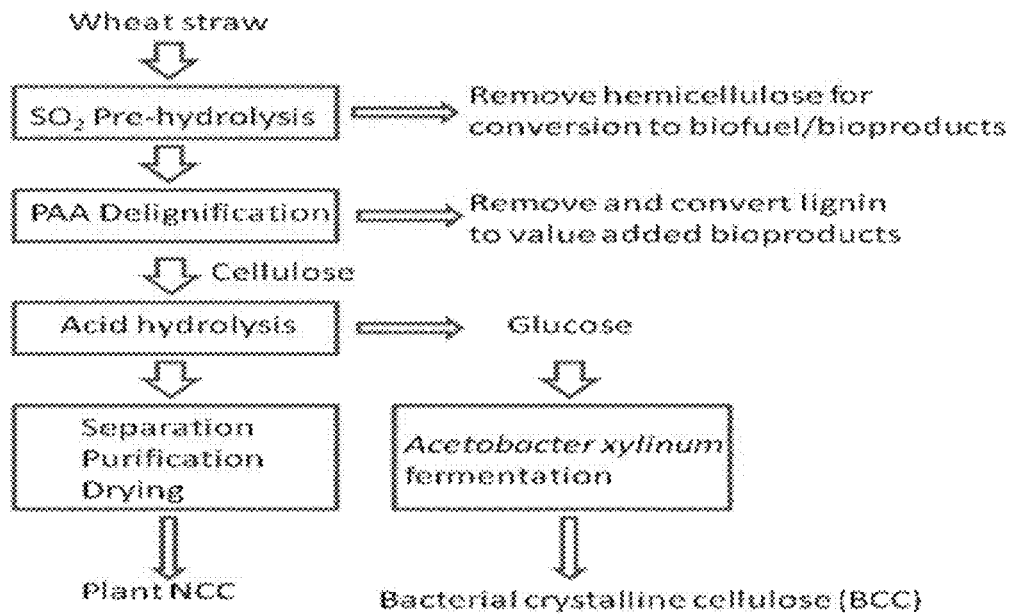
FIG. 5 is a schematic representation of a process for isolating cellulose nanocrystals according to an embodiment.

As represented in FIG. 5, high-quality NCC may be obtained from biomass raw materials. Biomass is biological material from living, or recently living organisms. Biomass may include such things as forest residues (such as dead trees, branches and tree stumps), yard clippings, wood chips and municipal solid waste. Biomass may also include cultivated plants, such as miscanthus, switchgrass, hemp, corn, wheat straw, poplar, willow, sorghum, sugarcane, bamboo, and a variety of tree species, ranging from eucalyptus to oil palm.

The representation of FIG. 5 shows wheat straw as the starting material, but the starting material could be any of the materials as provided above, as well as other biomass materials which contain cellulose. As shown in FIG. 5, the first step in manufacturing NCC is to remove hemicelluloses from the plant biomass. Hemicellulose may be hydrolyzed by several methods, including acids and enzymes. Hemicellulose may also be hydrolyzed by using sulfur dioxide ($SO_2$). Sulfur dioxide ($SO_2$) is a gas that can be used as a catalyst for the hydrolysis of hemicellulose oligomers. In addition, because it is a gas, $SO_2$ may be recovered downstream of the hydrolysis process and be reused to significantly reduce operational costs. As indicated in FIG. 5, $SO_2$ hydrolysis may be applied for extraction of hemicellulose from the biomass, while also enabling the hemicellulose to be recovered as monosaccharides that are readily available for biofuel production. High yields of hemicelluloses may be extracted in this manner, especially from hardwood chips.

After removing the hemicellulose, the resultant cellulosic product may be treated to remove the lignin. Lignin removal may be achieved using several methods, including alkaline hydrolysis with sodium hydroxide, calcium hydroxide, or ammonia. As shown in FIG. 5, lignin may also be removed with peracetic acid (PAA) treatment. PAA based pretreatment can be useful in eliminating agricultural biomass lignin, while also converting biomass lignin to value added phenolic compounds which may be recycled for animal feed and adhesive applications.

After the PAA delignification, a pure cellulose substrate may be obtained. The extraction of NCC from this substrate may be carried out by an additional hydrolysis step, which may be an acid hydrolysis. As shown in FIG. 5, this hydrolysis may be done by using sulfuric acid ($H_2SO_4$). The acid hydrolysis degrades the amorphous regions of cellulose nanofibrils and leaves the crystalline cellulose. The crystalline cellulose may be separated, purified and dried. During this hydrolysis, a significant portion of the cellulose may be converted to soluble sugars that may be recovered for additional uses by removing the acid therefrom. The acid may be removed by a process, such as a membrane fractionation process that may effectively separate sugar from the $H_2SO_4$. The recovered sugar stream may be used for culturing *Acetobacter xylinum*, which, in turn, may be used to produce additional crystalline cellulose (bacterial crystalline cellulose (BCC)).

Figure 6:
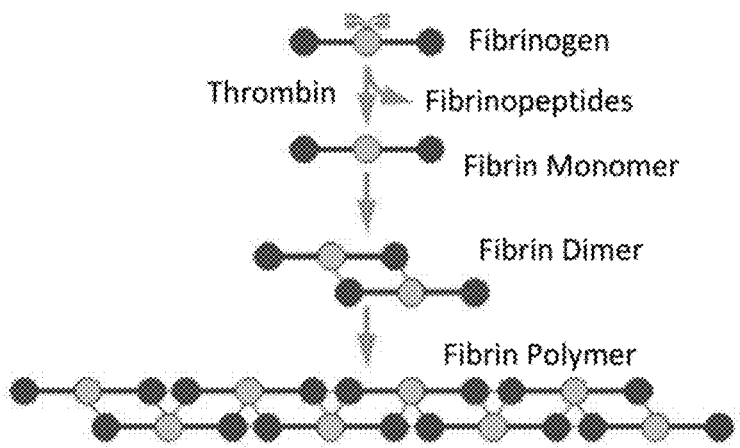
FIG. 6 depicts a simplified schematic representation for the formation of fibrin from fibrinogen according to an embodiment.

As disclosed herein, a nanocomposite may be formed by combining the cellulose nanocrystals with fibrin to provide the desired qualities of both strength and elasticity. Fibrin is a fibrous, non-globular protein found in blood and is involved in the clotting of blood. As represented in FIG. 6, fibrin is formed from fibrinogen by the protease thrombin, and polymerizes to form a mesh-like structure. Fibrin has good elasticity but lacks strength and stability when subjected to a physiological environment, and therefore lacks the appropriate mechanical properties specifically required for synthetic grafts, such as, for example, a vascular graft.

Figure 7:
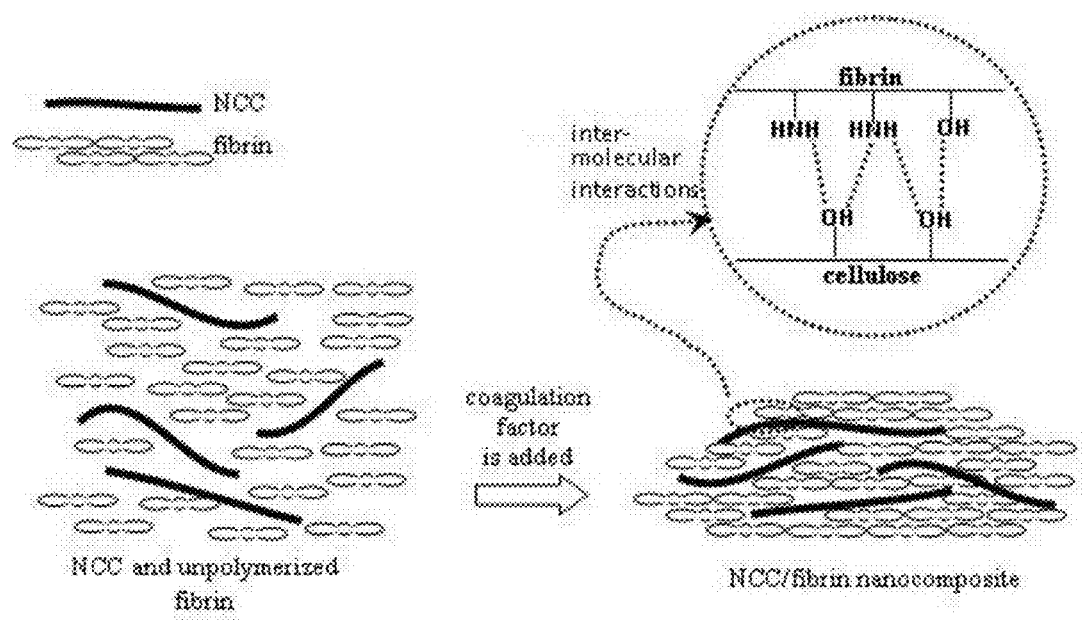
FIG. 7 depicts a simplified schematic representation for the formation of a nanocrystalline cellulose/fibrin nanocomposite according to an embodiment.

The illustration provided by FIG. 7 represents an embodiment of a biomaterial produced by coagulation of fibrinogen in the presence of NCC to produce a fibrin matrix containing and cross-linked with NCC. Fibrinogen is the precursor to fibrin, and may be obtained commercially or may be harvested from a patient's own blood to culture an autologous fibrin. Fibrinogen, unlike fibrin, is soluble in water and other aqueous solutions such as physiological buffers. NCC, as discussed previously, may be extracted from different native celluloses. NCC may be suspended in a solution, such as a physiological buffer, and may be well-dispersed in aqueous solutions through ultrasonication.

In the embodiment of FIG. 7, upon formation of the fibrin matrix, the NCC may be cross-linked with the fibrin by means of hydrogen bonds, represented by the dotted lines in the enlarged view. The molecular interactions of NCC and fibrin within the nanocomposite thereby provide strength to the elastic yet brittle fibrin matrix. In various configurations, the composition of the nanocomposite may be altered to vary the ratio (by weight) of NCC to fibrin in the nanocomposite, to thereby alter the mechanical properties (strength, elasticity) of the nanocomposite to match the diverse properties of various native graft materials. In an embodiment, the ratio by weight of NCC to fibrin may be about 0.01:1 to about 10:1. A larger ratio of NCC to fibrin may produce a nanocomposite of higher strength, while a lower ratio of NCC to fibrin may produce a nanocomposite of increased elasticity. As an example, a nanocomposite may be configured to have similar elasticity and strength properties as those exhibited by a 5 mm blood vessel which is to be replaced.

In an embodiment, after determining the desired strength and elasticity of the nanocomposite product, appropriate amounts of NCC, fibrinogen and thrombin may be combined in an aqueous solution. The ingredients may be thoroughly mixed by a method such as ultrasonication. Under appropriate reaction conditions, the thrombin will cause the fibrinogen to form the fibrin matrix incorporating the NCC therein. The nanocomposite may also be shaped to match a shape of the tissue which it is to replace. For a sheet-like graft material, the aqueous solution may be spread to a desired thickness on a planar surface, which may be of a material such as silicon to prevent sticking. Alternatively, the solution may be poured into a form, or mold, also of a material to prevent sticking, such as silicon, and having the desired shape which the final material is to have.

Figure 8:
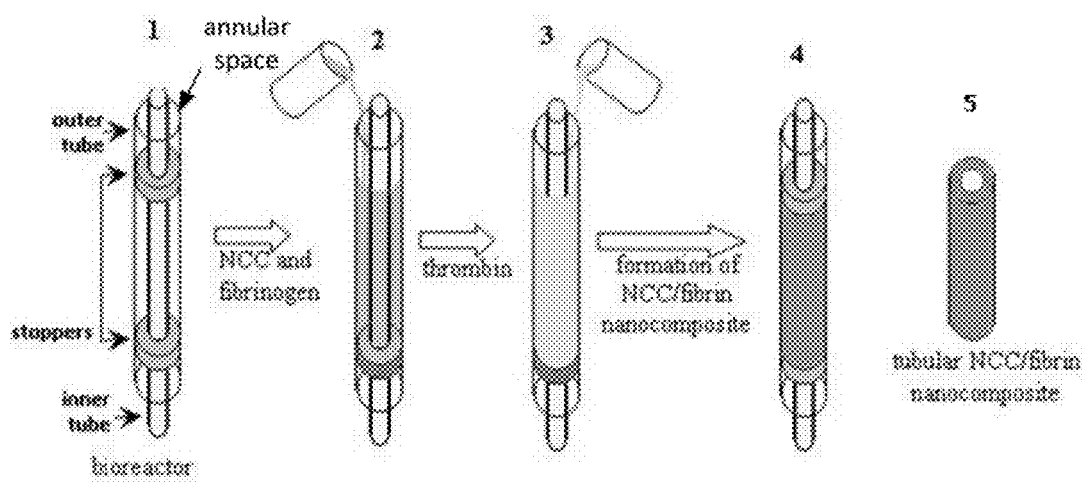
FIG. 8 depicts the formation of a tubular nanocomposite according to an embodiment.

In an embodiment, a tubular graft may be produced by a method as illustrated in FIG. 8. As illustrated in FIG. 8-1, a bioreactor/form may be constructed by inserting a first tubular member inside a larger tubular member to define an annular space therebetween. The tubular members may be of a material, such as silicon, which will prevent adherence of the nanocomposite thereto, while being gas-permeable to allow gas flow to and from the annular space. Alternatively, the tubes may be of any other material and have a non-stick coating on the surfaces thereof. In an additional embodiment, the inner member may be a solid cylindrical member instead of a tube.

The inner tubular member may have a diameter selected to match the inner diameter of the blood vessel which is to be replaced, and the outer tubular member may be configured in conjunction with the inner tubular member to provide an annular space that will give the cylindrical wall of the tubular graft a thickness that may at least match a thickness of the blood vessel wall that is to be replaced. In an embodiment, the thickness of the cylindrical wall may be configured to match, or be greater than the thickness of the blood vessel wall that is to be replaced.

In various embodiments, various combination of silicone tube sizes may be used to produce various diameters and wall thicknesses of tubular-shaped nanocomposites. The tubular nanocomposites may have inner diameters of about 1 mm to about 25 mm. In an embodiment, the inner diameters of the tubular nanocomposites may be about 1 mm to about 6 mm, and as examples, the inner diameter may be about 1 mm, about 1.5 mm, about 2 mm, about 2.5 mm, about 3 mm, about 3.5 mm, about 4 mm, about 4.5 mm, about 5 mm, about 5.5 mm, about 6 mm, or any size between any two of the listed values.

At least one stopper may be provided between the tubes for containment of a liquid between the tubes. An additional stopper may be provided to provide a protective cover once the space is filled to a desired level.

Appropriate amounts of NCC and fibrinogen may be suspended in a cold physiological buffer. A ratio, by weight, of the amounts of NCC to fibrinogen may be about 0.1:1 to about 5:1. As mentioned above, the ratio of the amounts of NCC and fibrinogen in the mixture may be varied to manipulate the mechanical properties and other properties of the nanocomposite being produced. The NCC and fibrinogen may be suspended in an appropriate volume of buffer solution to produce a mixture which may be from about 0.005 grams of NCC/fibrinogen in about 1 ml buffer to about 0.010 grams of NCC/fibrinogen in about 1 ml buffer.

The temperature of the buffer solution and suspended solids may be at a temperature which mimics physiological body temperature or about 36° C. to about 38° C. The buffer may be, for example, trisbuffered saline (TBS), phosphate buffered saline (PBS) and physiological saline solution. The mixture may be mixed, for example by ultrasonication, to disperse the NCC and fibrinogen in the buffer solution.

As shown in FIG. 8-2, the NCC/fibrinogen solution may be poured into the annular space between the outer and inner cylinders of the bioreactor to a height required to produce a length of tubing at least sufficient to replace the vessel in need of repair. The temperature of the mixture in the bioreactor may be kept considerably within human body temperature (a few degrees above or below about 37° C.).

The thrombin may also be suspended in a physiological buffer, such as: trisbuffered saline (TBS), phosphate buffered saline (PBS), or physiological saline solution. This thrombin solution may have about 0.005 g thrombin in about 1 ml buffer to about 0.10 g thrombin an about 1 ml buffer, so that when added to the fibrinogen, the weight ratio of thrombin to fibrinogen may be about 1:1 to about 5:1. As depicted in FIG. 8-3, the thrombin solution may be added into the NCC/fibrinogen mixture in the annular space in the bioreactor to initiate the formation of fibrin. The thrombin may be distributed through the mixture by ultrasonication.

The temperature of the reactant mixture in the bioreactor/form may be adjusted to a temperature of about 36° C. to about 38° C. and the reaction may be allowed to proceed for at least about 1 hr, to allow the fibrin matrix to form around and incorporate the NCC therein, thereby forming the nanocomposite vascular graft, as shown in FIG. 8-4.

The tubular nanocomposite may be taken out of the bioreactor/form, as shown in FIG. 8-5 and stored in a physiological salt solution or PBS. The salt solution may be about 0.9% sodium chloride or potassium chloride in water. The tubular nanocomposite may be prepared at least about 24 hours prior to the time in which it is to be used to provide an appropriate storage time which is sufficient to allow for compaction before proceeding to further processes. In this manner, compaction allows for a tightening or condensing of interstitial space of the walls of the nanocomposites to make the material more dense and also decreasing the size of the initial tubular form.

Further treatment to the nanocomposite may be performed if needed. Some examples of additional treatments may include but are not limited to: treating the nanocomposite with crosslinkers, such as glutaraldehyde and dextran, or coating the outer wall of the nanocomposites with cultured endothelial cells.

Figure 9:
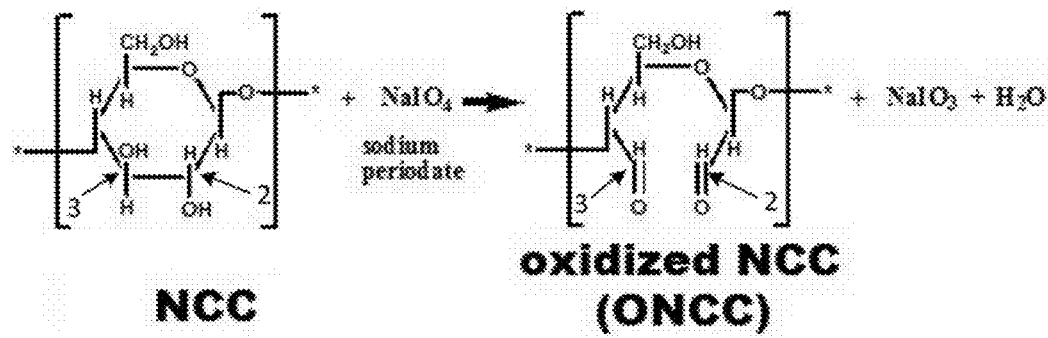
FIG. 9 depicts an alternative nanocomposite using oxidized nanocrystalline cellulose according to an embodiment.
Figure 9:
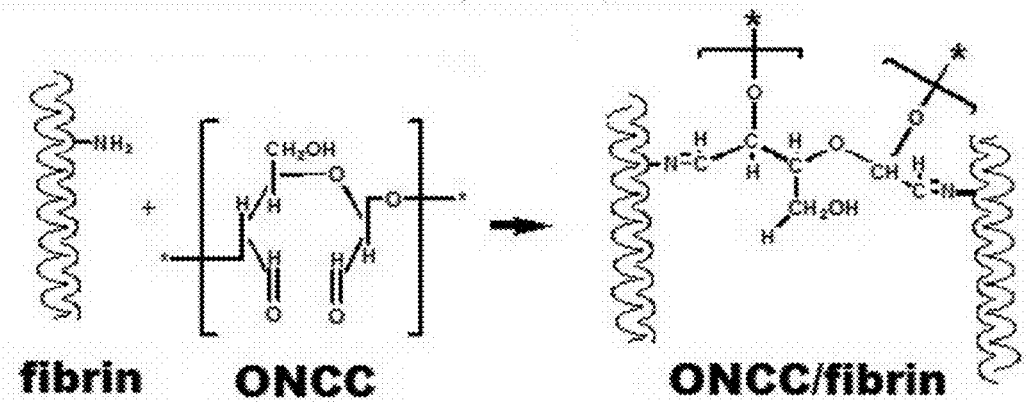

In an additional embodiment, as represented by FIG. 9, the NCC may be oxidized prior to incorporation of the NCC into the fibrin matrix. As discussed above, and depicted in FIGS. 2 and 5, cellulose is formed of linear chains of repeating saccharide units. As shown in FIG. 9, carbon atoms 2 and 3 of a saccharide unit may be oxidized to produce a C=O at carbon atoms 2 and 3. The oxidation may be performed by any of a variety of methods, including but not limited to periodate oxidation or 2,2,6,6-tetramethylpiperidine-1-oxyl radical (TEMPO) oxidation. As represented in FIG. 9, the oxidation may be done by exposure of the NCC to sodium periodate ($NaIO_4$). The NCC may be oxidized so that at least one of carbon atom 2 and carbon atom 3 of at least one saccharide unit of at least one linear chain may be oxidized to produce oxidized nanocrystalline cellulose (ONCC). The amount of oxidation may be varied by controlling the amount of time in which the NCC is exposed to the oxidizing agents. For example, NCC exposed to $NaIO_4$ for a period of time of about 4 hours will have more C=O formations at carbon atoms 2 and 3 than NCC which oxidized for a period of time of about 1 hour.

Oxidation of NCC to produce ONCC may be done under the following conditions: oxidation temperature—about 20° C. to about 200° C.; oxidation chemicals—metal salts of periodic acid, such as sodium periodate, at a minimum dosage of about 0.01 g per gram of NCC; oxidation time—about 10 minutes to about 48 hours. In an embodiment, the oxidation time may be about 0.5 hours to about 8 hours. In an embodiment, a degree of oxidation (the amount of carbonyl per 100 cellobiose units) may range from about 0 to about 50. In an embodiment, the oxidation may be from about 2 to about 8. For comparison, the degree of oxidation was determined for several samples: wheat straw/NCC—0; 4 hr-ONCC—3.4; 6 hr-ONCC—4.2; 8 hr-ONCC—7.8; 12 hr-ONCC—15.1; 24 hr-OCel—15.4.

In a manner as discussed above for NCC, the ONCC may similarly be incorporated into a fibrin matrix by combining the ONCC with fibrinogen and subjecting the mixture to thrombin to form a fibrin matrix. However, with ONCC, imine linkages (C=N) may form between any oxidized carbon atoms 2 and 3 and nitrogens of the fibrin, covalently bonding the ONCC with the fibrin. A stronger cross-linking will therefore be present, as the matrix material may now include both covalent bonds and hydrogen bonds between the fibrin and the ONCC as shown in FIG. 9.

Figure 11:
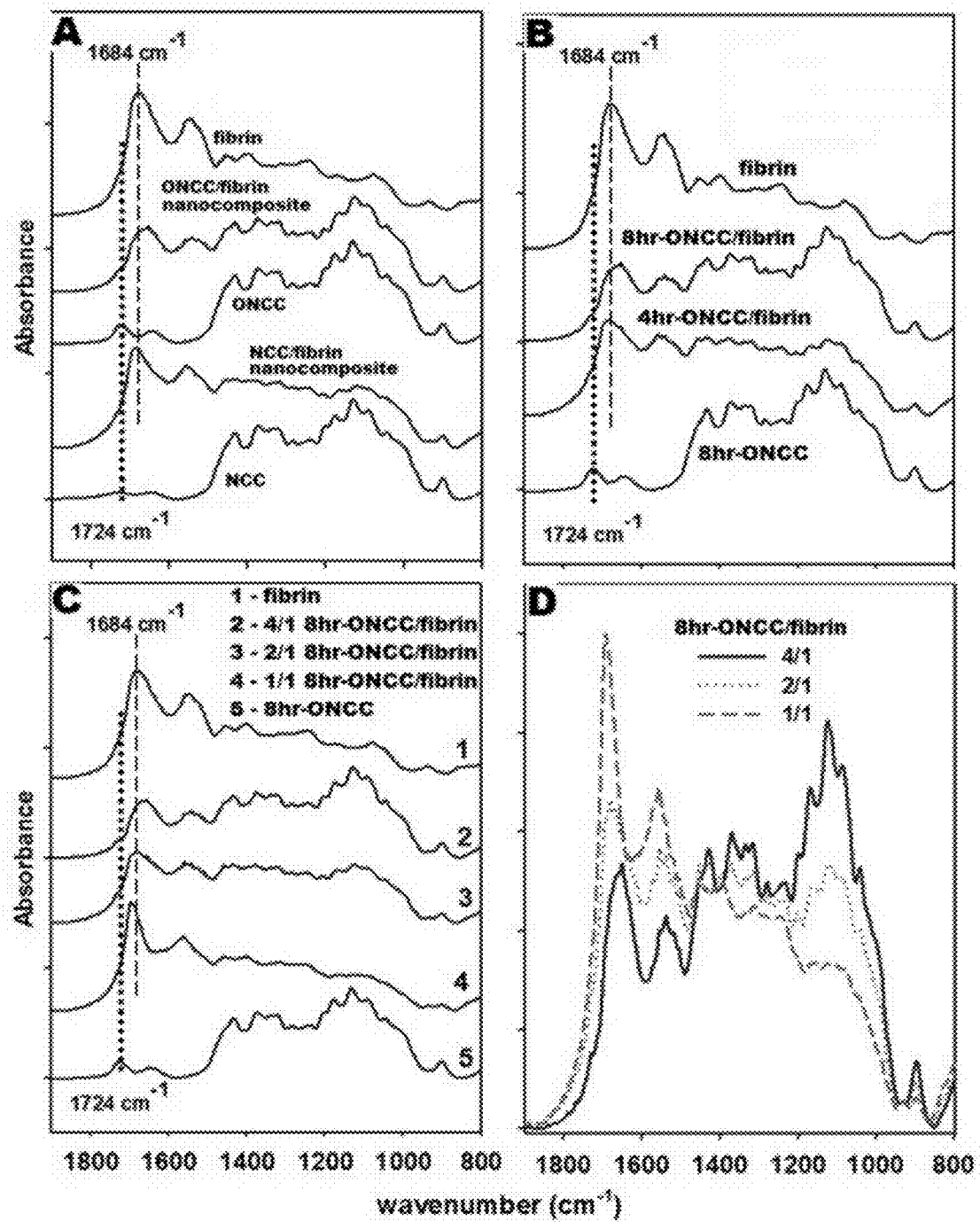
FIG. 11 presents FTIR spectral results comparing nanocomposites with native precursors according to an embodiment.

Various compositions of nanocomposites having weight ratios of about 1:1 NCC/fibrin and about 1:1, about 2:1 and about 4:1 ONCC/fibrin were tested and compared with porcine coronary artery (PCA) as well as native samples of fibrin, NCC and ONCC. The indication of 4 hr, 6 hr and 8 hr (in FIGS. 11-12) indicates the approximate length of time of oxidation of the ONCC.

FIGS. 11A-11D show comparison FTIR (Fourier Transform Infra Red) spectra of samples of NCC, ONCC, fibrin and nanocomposites of NCC/fibrin and ONCC/fibrin, with a focus on the C=O absorbance intensity at 1684 $cm^{-1}$ and 1724 $cm^{-1}$ and an absorbance of the nanocomposite at about 1100 $cm^{-1}$. FIG. 11A shows a comparison of native samples of NCC, fibrin, oxidized NCC (8 hr-ONCC), nanocomposite (NCC/fibrin) and nanocomposite (2/1 8 hr-ONCC/fibrin). FIG. 11B shows a comparison of nanocomposites with NCC of various oxidation times. FIG. 11C shows a comparison of samples with various ONCC compositions. FIG. 11D shows ONCC absorbance intensities at 1800-800 $cm^{-1}$ with various ONCC compositions.

As shown in FIG. 11A, fibrin has a distinctive absorbance at 1684 $cm^{-1}$, owing to its antiparallel β-sheet structure, while NCC has a minor perceptible band at 1636 $cm^{-1}$, representing H—OH bending vibration of adsorbed water molecules. FIG. 11A shows the differences in spectra between the NCC/fibrin and the ONCC/fibrin nanocomposites. Nanocomposite formed between non-oxidized NCC and fibrin predominantly exhibit absorbance bands that are almost identical to fibrin, the absorbance bands of NCC between 1500-800 $cm^{-1}$ is not apparent in this nanocomposite (FIG. 11A). There is no significant shift on all the peaks and no new band that appeared. This suggests that there is no significant molecular interaction between non-oxidized NCC and fibrin. The FTIR spectrum of nanocomposite formed between ONCC and fibrin shows a broadening of a peak at 1660 $cm^{-1}$ which is shifted from both 1684 $cm^{-1}$ (from fibrin) and 1636 $cm^{-1}$ (from NCC). The 1660 $cm^{-1}$ band is a characteristic absorption band of imine (C=N). The peak at 1724 $cm^{-1}$ of ONCC, which represents the C=O formed from oxidation, disappears in the spectrum of the ONCC/fibrin nanocomposite. This evidence substantiates the formation of imine group between carbonyl group in ONCC and amines in fibrin.

FIG. 11B shows the differences of the molecular interactions of the nanocomposites that were composed of NCC with varying degrees of oxidation. Again, the peak at 1724 $cm^{-1}$ of ONCC disappears in all nanocomposites due to the transformation of carbonyls to imines. From 1684 $cm^{-1}$ of fibrin and 1636 $cm^{-1}$ of NCC, the peaks of 4 hr- and 8 hr-ONCC/fibrin nanocomposites shift to 1678 and 1660 $cm^{-1}$ respectively. There is a peak broadening following the order of fibrin <4 hr-ONCC/fibrin nanocomposites <8 hr-ONCC/fibrin nanocomposites with a peak width determined at the half maximum height of 61.7, 62.7 and 68.5 $cm^{-1}$ respectively. An increase in imine group typically leads to a wider peak between 1690 and 1640 $cm^{-1}$, therefore, an increase in oxidation time resulted in increasing imine group formation in ONCC/fibrin nanocomposites. FIGS. 11C-D follows the FTIR spectra of 8 hr-ONCC/fibrin nanocomposites with varying compositions. As the ratio of ONCC to fibrin increases, the widening of the peak at ~1660 $cm^{-1}$ also increased. The characteristic peaks of NCC between 1500 $cm^{-1}$ and 800 $cm^{-1}$ also gradually became distinct (FIG. 11D), indicating that increasing amount of ONCC was integrated into the fibrin matrix.

A mechanical property of the NCC/fibrin or ONCC/fibrin nanocomposites, burst pressure, was tested. The burst test was done with a simple tester where a sample, in a sheet form, was mounted to a sample mount connected to a t-connector with a syringe used to apply air pressure and a pressure transducer to read the burst pressure. Sample burst pressure values (psi) were measured: Fibrin—0.05; 1/1 NCC/fibrin—0.06; 1/1 8 hr-ONCC/fibrin—1.14; 2/1 8 hr-ONCC/fibrin—0.94; Normal human blood pressure—1.5/2.3 (80/120 mmHg).

Figure 10:
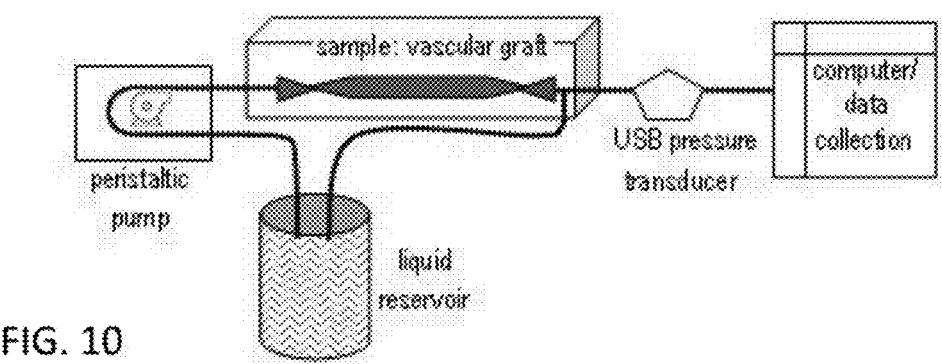
FIG. 10 is a representative illustration of a testing system for testing tubular nanocomposites according to an embodiment.
Figure 12:
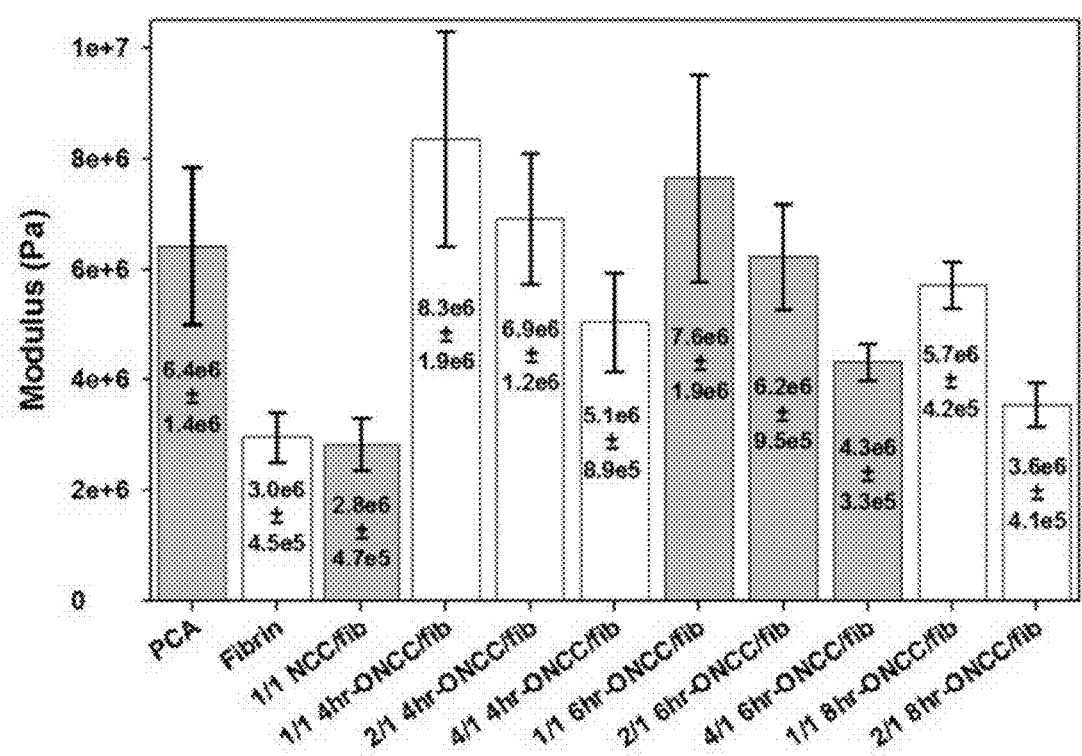
FIG. 12 provides modulus results comparing nanocomposites and native precursors according to an embodiment.

An integrated mechanical tester is illustrated in FIG. 10. For this tester, a tubular form sample will be tested, providing information on the geometry-dependent mechanical properties. In addition, time-dependent mechanical properties such as durability can also be obtained by performing an accelerated mechanical straining on the sample. The tester in FIG. 10 will be composed of a programmable peristaltic pump to apply pressures into a sample tube by filling it with physiological salt solution. The pressure inside the sample tube will be monitored by the pressure transducer, and the measurements will be collected and saved in a computer. Additional testing of the mechanical properties were performed by a Digital Instruments Multimode Nanoscope III atomic force microscope (AFM). Force imaging was performed with the 10×10×1 mm sample submerged in PBS. From the obtained AFM force curve, the modulus of the tested specimen was calculated using Hertz-Sneddon method and the result is shown in FIG. 12. As can be seen in the graphed results, the moduli of 1/1 and 2/1 4 hr-ONCC/fibrin and 6 hr-ONCC/fibrin and 1/1 8 hr-ONCC/fibrin nanocomposites are comparable to or higher than the modulus of the native blood vessel, porcine coronary artery (PCA). It shows that ONCC has reinforced the fibrin matrix effectively as seen by the significant increase in the modulus of the nanocomposites compared to the pure fibrin.

Nanocomposites of crystalline cellulose and fibrin may be produced that have mechanical properties similar to, or even better than the mechanical properties of native blood vessels. Tubular nanocomposites of crystalline cellulose and fibrin may, therefore, provide improved artificial vascular graft application. In addition, the nanocomposites may also be produced in different forms and may be used as grafts for other tissues, as well as for a material for internal organ replacement or scaffolds (e.g. heart valve, brain membrane).

EXAMPLE 1

Production of NCC/ONCC

Nanocrystalline cellulose will be produced from wheat straw biomass. The biomass will be placed in a reactor vessel and hydrolyzed with $SO_2$ gas to hydrolyze the hemicellulose into monosaccharides. The monosaccharides will be recovered and recycled into biofuel. The biomass will then be treated with peracetic acid to break down the lignin into corresponding phenolic compounds. The phenolic compounds will be recovered and recycled as a feed additive. The remaining mass will then be essentially pure cellulose which will be milled and turned into pulp to reduce the cellulose to its constituent nanofibrils. The nanofibrils will be hydrolyzed with sulfuric acid to break apart the amorphous cellulose regions, leaving the crystallized cellulose intact. The amorphous cellulose regions will be broken down into glucose in the process, and the glucose may be separated from the sulfuric acid for reuse. The glucose will be recycled as feed for bacteria cultures of *Acetobacter xylinum*, which is a bacteria that is capable of producing nanocrystalline cellulose.

The nanocrystalline cellulose will be oxidized at about 100° C. by adding sodium periodate into a reaction mixture with the NCC at a rate of about 0.01 g of sodium periodate per gram of NCC. The oxidation will be performed for about 6 hours, and the ONCC will be separated and purified.

EXAMPLE 2

A Biomaterial Graft of NCC/Fibrin

A sheet of biomaterial will be prepared from crystalline cellulose and fibrin having a composition ratio, by weight, of about 1:1 NCC to fibrin. About 0.010 g of the NCC and 0.010 g of fibrinogen will be suspended in about 2 ml of trisbuffered saline (TBS) which has been maintained at a temperature of about 37° C., and the mixture will be subjected to ultrasonication for about 60 seconds to thoroughly mix the constituents.

About 0.010 g of thrombin (or 1 ml of a thrombin/buffer solution of 0.010 g of thrombin in 1 ml of TBS buffer) will be added to the mixture and the mixture will again be subjected to ultrasonication for about 60 seconds to thoroughly mix the constituents. The mixture will be poured onto a planar silicon surface to produce a layer of about 1 mm thickness, which will be placed in a chamber heated to about 37° C. for about 12 hours to initiate formation of a fibrin matrix that will form around and bind NCC by hydrogen bonds.

After the specified period of time, the resultant graft material will be washed and stored in a physiological saline solution.

EXAMPLE 2

An ONCC/Fibrin Polymer

A sheet of polymer material will be prepared from crystalline cellulose and fibrin having a composition ratio, by weight, of about 1:1 ONCC to fibrin. About 0.010 g of NCC will be suspended in about 1 ml of water. About $6 \times 10^{-4}$ g of sodium periodate will be added to the NCC suspension and the resultant oxidation reaction will be conducted for about 4 hours. Oxidized NCC will be filtered from the solution.

About 0.010 g of the ONCC and 0.010 g of fibrinogen will be suspended in about 2 ml of trisbuffered saline (TBS) which has been cooled to a temperature of about 37° C., and the mixture will be subjected to ultrasonication for about 60 seconds to thoroughly mix the constituents.

About 0.010 g of thrombin (or 1 ml of a thrombin/buffer solution of 0.010 g of thrombin in 1 ml of TBS buffer) will be added to the mixture and the mixture will again be subjected to ultrasonication for about 60 seconds to thoroughly mix the constituents. The mixture will be poured onto a planar silicon surface to produce a layer of about 1 mm thickness, which will be placed in a chamber heated to about 37° C. for about 12 hours to initiate and enable the formation of a fibrin matrix with covalent cross-linking with the ONCC.

After the specified period of time, the resultant sheet will be washed and stored in a physiological saline solution.

EXAMPLE 3

A Tubular Vascular Graft

A tubular graft having a length of about 5 cm, an internal diameter of about 4 mm, and an external diameter of about 6 mm will be prepared from crystalline cellulose and fibrin having a composition ratio, by weight, of about 1:1 ONCC to fibrin. The ONCC will be prepared as above in Example 2.

A bioreactor/form for producing a tubular graft material will be produced by inserting a first silicon tube having an outer diameter of about 4 mm inside a second silicon tube having an internal diameter of about 10 mm (extra space is needed for the solution to form the nanocomposites. A bottom end of the tubing arrangement will be sealed for retaining fluid in the annular space formed between the tubes.

About 0.050 g of the ONCC and 0.050 g of fibrinogen will be suspended in about 10 ml of trisbuffered saline (TBS) which has been cooled to a temperature of about 37° C., and the mixture will be subjected to ultrasonication for about 60 seconds to thoroughly mix the constituents. About 10 ml of the resultant mixture will be poured into the annular space of the prepared bioreactor/form to a height of about 5 cm from the bottom seal.

A thrombin/buffer solution of 0.50 g of thrombin in 5 ml of TBS buffer will be prepared separately, and about 5 ml will be injected into the mixture in the annular space of the bioreactor. A seal will be placed on the upper end of the bioreactor, and the bioreactor will be subjected to ultrasonication for about 60 seconds to thoroughly mix the constituents. The bioreactor will be heated to about 37° C. for about 12 hours to initiate and enable formation of a fibrin matrix with covalent cross-linking with the ONCC.

After the specified period of time, the resultant tubular graft formed in the annular space will be removed from the bioreactor and stored in a physiological saline solution.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method for producing nanocrystalline cellulose from biomass, the method comprising:
    extracting hemi-cellulose from the biomass to produce a first biomass portion and a first extract;
    extracting lignin from the first biomass portion to produce a cellulose portion and a second extract;
    processing the cellulose portion into cellulose nanofibrils, the nanofibrils comprising nanocrystalline cellulose separated by regions of amorphous cellulose, wherein the processing the cellulose portion comprises milling of the cellulose portion into a pulp;
    hydrolyzing the amorphous cellulose in the nanofibrils to produce a solution of nanocrystalline cellulose and glucose; and
    separating the nanocrystalline cellulose from the glucose.

2. The method of claim 1, wherein the method further comprises oxidizing the nanocrystalline cellulose to produce oxidized nanocrystalline cellulose.

3. The method of claim 1, wherein:
    extracting the hemicellulose comprises hydrolyzing the hemi-cellulose in the presence of $SO_2$ to form monosaccharides; and
    the method further comprises removing the monosaccharides as the first extract.

4. The method of claim 1, wherein:
    extracting the lignin comprises breaking down the lignins with acid to produce phenolic compounds; and
    the method further comprises removing the phenolic compounds as the second extract.

5. The method of claim 1, wherein hydrolyzing the amorphous cellulose comprises hydrolyzing the amorphous cellulose in the presence of sulfuric acid.

6. The method of claim 5, further comprising:
    washing the glucose to remove sulfuric acid therefrom; and
    recycling the glucose by using the glucose as a food source for bacteria cultures to produce bacterial crystalline cellulose.

7. The method of claim 1, wherein extracting hemicellulose comprises extracting hemi-cellulose from the biomass selected from the group consisting of miscanthus, switchgrass, hemp, corn, wheat straw, poplar, willow, sorghum, sugarcane, bamboo, and combination thereof.

8. The method of claim 1, further comprising:
    recycling the first extract comprising hemi-cellulose into biofuel; and
    recycling the second extract comprising lignin to form phenolic compounds.

9. A method for producing a fibrin-nanocrystalline cellulose composite, the method comprising:
    mixing an aqueous solution of nanocrystalline cellulose and fibrinogen to produce a reactive mixture; and
    incubating the reactive mixture with thrombin to convert fibrinogen to fibrin and produce a composite material of cross-linked nanocrystalline cellulose and fibrin.

10. The method of claim 9, wherein amounts of the nanocrystalline cellulose, the fibrinogen and the thrombin in the total reaction mixture are in a ratio by weight of about 0.1:1:1 to about 5:1:1.

11. The method of claim 9, further comprising using the fibrin-nanocrystalline cellulose composite as a tissue graft for a tissue to be repaired.

12. The method of claim 9, wherein:
    the method further comprises oxidizing the nanocrystalline cellulose prior to mixing of the nanocrystalline cellulose and the fibrinogen.

13. The method of claim 9, wherein incubating the reactive mixture comprises incubating the reactive mixture with thrombin to produce the composite material of cross-linked nanocrystalline cellulose and fibrin, wherein the composite material has a ratio by weight of the nanocrystalline cellulose to the fibrin of about 0.1/1 to about 10/1.

14. The method of claim 9, further comprising treating the fibrin-nanocrystalline cellulose composite material with cross-linking agents.

* * * * *

UNITED STATES PATENT AND TRADEMARK OFFICE
CERTIFICATE OF CORRECTION

PATENT NO. : 9,724,213 B2
APPLICATION NO. : 14/443867
DATED : August 8, 2017
INVENTOR(S) : Zhang et al.

Page 1 of 1

It is certified that error appears in the above-identified patent and that said Letters Patent is hereby corrected as shown below:

In the Specification

In Column 12, Line 25, delete "recitation no" and insert -- recitation, no --, therefor.

In Column 12, Line 47, delete "general such" and insert -- general, such --, therefor.

In Column 12, Line 54, delete "general such" and insert -- general, such --, therefor.

In the Claims

In Column 14, Line 21, in Claim 7, delete "and combination" and insert -- and any combination --, therefor.

Signed and Sealed this
Thirty-first Day of October, 2017

Joseph Matal
*Performing the Functions and Duties of the
Under Secretary of Commerce for Intellectual Property and
Director of the United States Patent and Trademark Office*